US011096578B2

(12) United States Patent
Hastie

(10) Patent No.: US 11,096,578 B2
(45) **Date of Patent: *Aug. 24, 2021**

(54) DEVICE COMPRISING AN OVERLAY MECHANISM, SYSTEM WITH DEVICES EACH COMPRISING AN OVERLAY MECHANISM WITH AN INDIVIDUALLY PROGRAMMABLE DELAY OR METHOD FOR OVERLAYING DATA

(71) Applicant: Infineon Technologies AG, Neubiberg (DE)

(72) Inventor: Neil Stuart Hastie, Lydney (GB)

(73) Assignee: Infineon Technologies AG, Neubiberg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/874,763

(22) Filed: May 15, 2020

(65) Prior Publication Data

US 2020/0275836 A1 Sep. 3, 2020

Related U.S. Application Data

(63) Continuation of application No. 15/711,391, filed on Sep. 21, 2017, now Pat. No. 10,653,315.

(30) Foreign Application Priority Data

Sep. 22, 2016 (DE) ......................... 102016218280.3

(51) Int. Cl.
*A61B 5/00* (2006.01)
*G06F 12/06* (2006.01)
(Continued)

(52) U.S. Cl.
CPC .......... *A61B 5/0006* (2013.01); *A61B 5/0031* (2013.01); *A61B 5/02055* (2013.01);
(Continued)

(58) Field of Classification Search
None
See application file for complete search history.

(56) References Cited

U.S. PATENT DOCUMENTS

2005/0262323 A1* 11/2005 Woo ...................... G06F 13/161 711/167
2007/0061500 A1* 3/2007 Gould ................. G06F 12/0623 711/103
(Continued)

FOREIGN PATENT DOCUMENTS

JP 2003005996 A 1/2003

OTHER PUBLICATIONS

Fang, Yi-Chiun et al. "Emulation of Object-Based Storage Devices by a Virtual Machine*." C.-H. Hsu et al. (Eds.): ICA3PP 2010, Part II, LNCS 6082, pp. 166-177, 2010.
(Continued)

*Primary Examiner* — Charles Rones
*Assistant Examiner* — Jonah C Krieger
(74) *Attorney, Agent, or Firm* — Eschweiler & Potashnik, LLC

(57) ABSTRACT

A device includes an overlay mechanism, system with devices each including an overlay mechanism with an individually programmable delay or method for overlaying data. A method for overlaying data includes redirecting an access which is directed to a first memory location to a second memory location. The method for overlaying data selectively delays access to the second memory location in case of a redirection by a time.

20 Claims, 4 Drawing Sheets

(51) Int. Cl.

| | |
|---|---|
| ***A61B 5/0205*** | (2006.01) |
| ***A61B 5/04*** | (2006.01) |
| ***G06F 16/22*** | (2019.01) |
| ***H04L 12/933*** | (2013.01) |
| ***G16H 10/60*** | (2018.01) |
| ***A61B 5/24*** | (2021.01) |
| ***A61B 5/316*** | (2021.01) |

(52) U.S. Cl.

CPC ................ *A61B 5/24* (2021.01); *A61B 5/316* (2021.01); *G06F 12/0638* (2013.01); *G06F 16/2272* (2019.01); *G16H 10/60* (2018.01); *H04L 49/101* (2013.01)

(56) References Cited

U.S. PATENT DOCUMENTS

2009/0106506 A1* 4/2009 Skerlj .................... G06F 12/02 711/154
2010/0023673 A1 1/2010 Struk
2013/0254487 A1* 9/2013 Tanaka ................. H04L 49/552 711/123
2014/0032512 A1 1/2014 Drew et al.
2014/0325129 A1 10/2014 Ahlquist

OTHER PUBLICATIONS

Griffin, John Linwood et al. "Timing-accurate Storage Emulation." Proceedings of the FAST 2002 Conference on File and Storage Technologies. Monterey, California, Jan. 28-30, 2002. 16 pages.

Non-Final Office Action dated Dec. 20, 2018 in connection with U.S. Appl. No. 15/711,391.

Final Office Action dated May 16, 2019 in connection with U.S. Appl. No. 15/711,391.

Notice of Allowance dated Jan. 27, 2020 in connection with U.S. Appl. No. 15/711,391.

* cited by examiner

| Target memory | Target Access Time (Cycles) | Overlay Access Time (Cycles) | Delay/Stall (cycles) to be added |
|---|---|---|---|
| Flash-1 | 12 | 10 | 2 |
| Flash-2 | 15 | 14 | 1 |
| Flash-3 | 21 | 15 | 6 |

| Target memory | Target Access Time (Cycles) | Overlay Access Time (Cycles) | Delay/Stall (cycles) to be added |
|---|---|---|---|
| Flash-1 | 12 | 15 | 0 |

| Redirecting an access which is directed to a first memory location to a second memory location | — S1 |

| Selectively delaying access to the second memory location in case of a redirection by a time | — S2 |

DEVICE COMPRISING AN OVERLAY MECHANISM, SYSTEM WITH DEVICES EACH COMPRISING AN OVERLAY MECHANISM WITH AN INDIVIDUALLY PROGRAMMABLE DELAY OR METHOD FOR OVERLAYING DATA

CROSS REFERENCE TO RELATED APPLICATIONS

This application is a continuation of U.S. patent application Ser. No. 15/711,391 which claims priority to German Patent Application number 10 2016 218 280.3 filed on Sep. 22, 2016 in the name of Neil Stuart Hastie, entitled "DEVICE COMPRISING AN OVERLAY MECHANISM, SYSTEM WITH DEVICES EACH COMPRISING AN OVERLAY MECHANISM WITH AN INDIVIDUALLY PROGRAMMABLE DELAY OR METHOD FOR OVERLAYING DATA" and is hereby incorporated in its entirety.

FIELD

Embodiments according to the disclosure are related to a device comprising an overlay mechanism. Further embodiments according to the disclosure are related to a system comprising at least two devices. Further embodiments according to the disclosure are related to a method for overlaying data.

SUMMARY

An embodiment according to the disclosure creates a device comprising an overlay mechanism configured or configurable to redirect an access which is directed to a first memory location to a second memory location. The overlay mechanism is configured or configurable to delay access to the second memory location in the case of a redirection.

Another embodiment according to the disclosure creates a system, comprising a first device as described above, wherein the first device comprises a first processor. The system also comprises a second device according to one of the preceding claims, wherein the second device comprises a second processor. The system comprises a bus structure comprising a plurality of bus segments and a plurality of memories. The first processor and the second processor are coupled with the memories via the bus structure. A delay of the overlay mechanism of the first device and a delay of the overlay mechanism of the second device are programmable individually.

A method for overlaying data comprises redirecting an access which is directed to a first memory location to a second memory location and selectively delaying access to the second memory location in case of a redirection by a time.

BRIEF DESCRIPTION OF THE DRAWINGS

Embodiments according to the disclosure will subsequently be described taking reference to the enclosed Figures in which.

DETAILED DESCRIPTION

Figure 1:
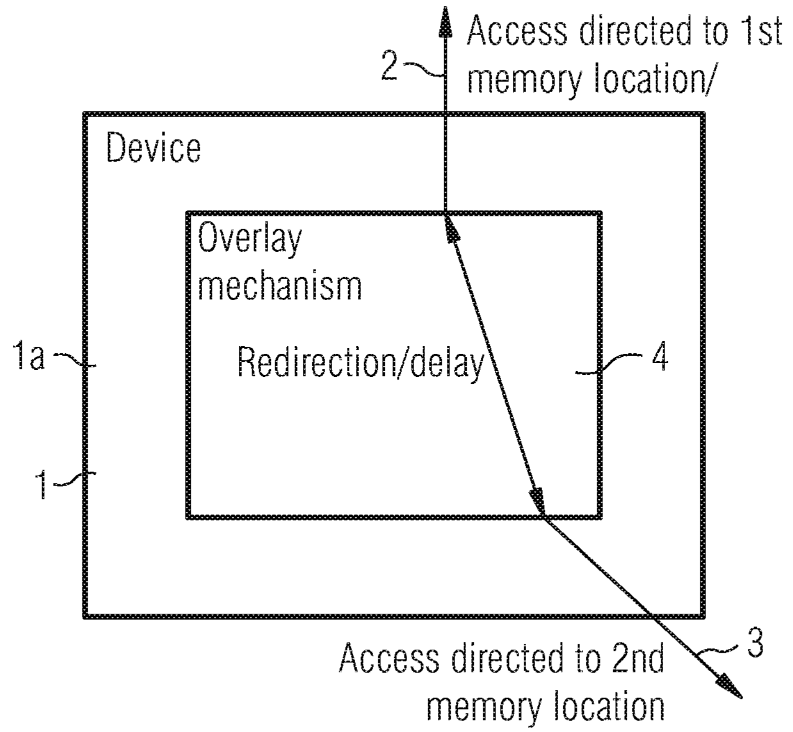
FIG. 1 illustrates schematically a device including the functional principle according a first embodiment, wherein the device comprises an overlay mechanism capable to perform a redirection of data and to delay an access to a second data location.

In FIG. 1 a first device 1 is illustrated having, for example, at least two external interfaces 2, 3. The first interface 2 is capable for an access directed to a first memory location and the second interface 3 is capable for an access directed to a second memory location. The interfaces to access the first and the second memory location 2, 3 may employ the same physical and/or logical structure which may be a bus. Within the device 1 there is an overlay mechanism 4 controlling or administrating an overlaying of data from a first memory location 5 to a second memory location 7. The overlay mechanism 4 may be used by a processor 1*a* being part of the device 1, and may, for example, be implemented using a sufficiently fast hardware circuit (or, alternatively, using a micro-programmed circuit or a processor). Thereby the change in a location of data is not visible or can be invisible to an application software. Thus, the application software can interact with the processor 1*a* during product development. The product development may, for example, comprise calibrating engine management systems. This can be technically implemented since the change in location of the data is performed by hardware within the device 1. The device 1 or the processor 1*a* may, for example, be controlled by a debug/calibration system or by an application software being part of the debug/calibration system. Also the application software may be executed on the device 1 or, more specifically, on the processor 1*a*.

The device 1 comprising the overlay mechanism 4 or the corresponding method for overlaying data may be controlled by the processor 1*a* within the device 1 requesting access to the first memory location. The overlaying mechanism 4 may be part of the processor 1*a* or may be a dedicated hardware associated with the processor (for example, coupled with the processor using a memory interface). The processor 1*a* itself may attempt to access data being stored in the first memory location. In signal or data processing, the processor 1*a* may forward a request to retrieve data being stored in the first memory location or to store data in the first memory location. Since, after redirection of data by the overlay mechanism 4, the data is retrieved from the first memory location or stored in the second memory location instead of the first memory location, the overlay mechanism 4 transforms a request of the processor to retrieve data from the first memory location into a request to retrieve data from the second memory location, wherein the second memory location may be in a physically different memory entity or memory range or memory structure when compared to the first memory location. Alternatively, a request of the processor 1*a* for data being stored in the first memory location may be transformed, by the overlay mechanism, to a request for data being stored in the second memory location. The overlay mechanism 4 is configured to or configurable to delay access to the second memory location in case of a redirection. In other words, in the case of a data read, the data obtained from the second memory location may, for example, be provided to the processor 1*a* with some intentionally inserted "extra" delay (which is longer than a physically unavoidable delay for retrieving data from the second memory location and for transporting the data from the second memory location to the overlay mechanism). In the case of a data write, a signaling to the processor that the data write is completed may, for example, be delayed (intentionally) by the overlay mechanism.

The delay of the overlay mechanism 4 of the device 1 may, for example, be programmable. Also the method may comprise programming a delay or target access time which may be applied at least to delay access to the second memory location. For instance a user or human user may be able to estimate a time for accessing the first memory location and the delay for accessing the second memory location. Since in this case the user is capable to estimate the access times, a user can calculate or estimate the additional delay of the overlay mechanism 4 or of the method for overlaying data, so that an access to the second memory location cannot be completed by the device 1 before (or faster than) an access to the first memory location would be possible.

Figure 2:
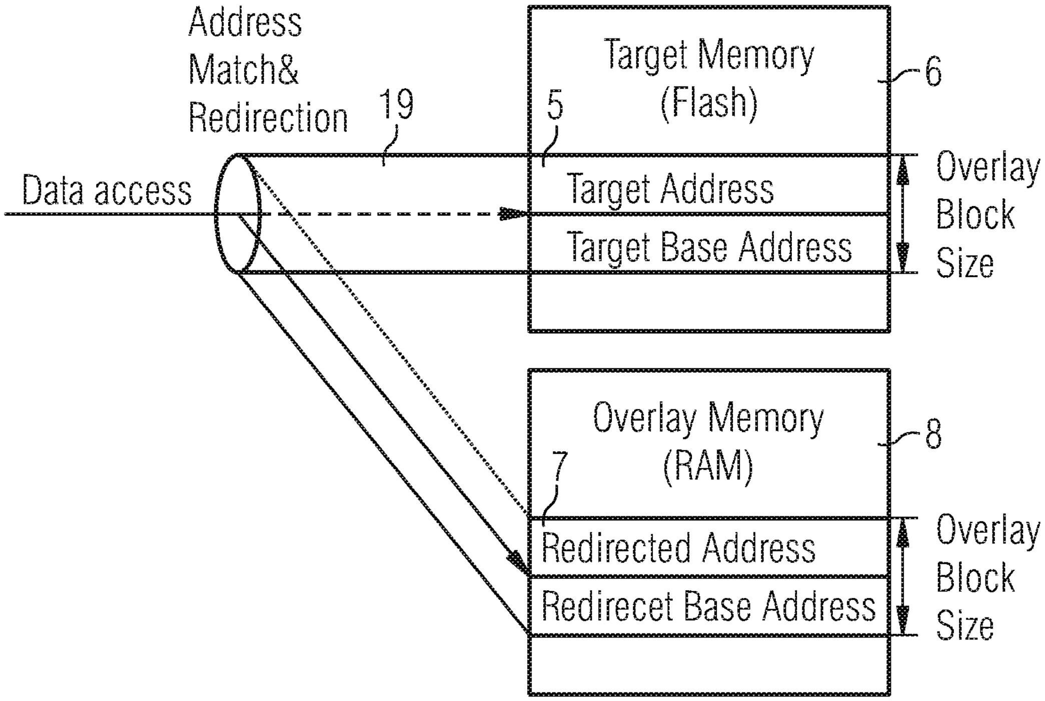
FIG. 2 illustrates schematically a second embodiment, wherein by means of a data access a target memory and an overlay memory can be accessed, wherein a data access may be overlayed from the target memory to the overlay memory.

As illustrated in FIG. 2 the first memory location 5 may be within a target memory 6 at which the device 1, especially a processor 1*a* which may be part of the device 1, may intend to store data (or from which the processor may retrieve data). Instead of storing data in the first memory location 5, the overlay mechanism 4 or a corresponding method for overlaying data stores data in a second memory location 7 being within an overlay memory 8. The (one or more) external interfaces 2, 3 may also access the respective target memory 6 and the respective overlay memory 8.

A memory location 5, 7 may by a bit, a byte or a number of bytes within one memory 6, 8. Alternatively a location 5, 7 may be an entire memory 6, 8. A location 5, 7 may be dividable in ranges being a part or a partition of a location. The first memory location 5 and the second memory location 7 may, under some circumstances, be part of the same memory 6, 8. In this case the target memory 6 and the overlay memory 8 are the same memory 6, 8. However, the first memory location and the second memory location are typically part of physically separate memories (for example, memories using different memory technologies and/or memories having different access times).

In the overlay mechanism 4 there may by a programmable table of target address ranges and an associated set of redirected address ranges to be substituted if a data access is performed to the target access range. Thereby the redirected address ranges are within the overlay memory 8 and/or in the second memory location 7. The change in location may not be visible to application software interacting with the device 1 but may be performed by hardware 4 within the device 1, preferably at request of the processor 1*a* within the device 1, under control of a debug/calibration system. The programmable table may be part of the hardware 4. The overlaying mechanism 4 is preferably implemented within hardware.

Hence, such a device 1 allows the logical translation of addresses without modification of application software. Hence, the device 1 allows, for example, the Flash data tables to be overlayed by the SRAM. The application software may rely on the device 1 for calibration purpose, for instance of an engine (or engine control software). The application software may (at least partially) be executed on the device 1 or processor 1*a*. In other words, for instance software for calibrating an engine is performed within the device 1 or by the processor 1*a* which outputs control parameters for an engine. In a real-world scenario, the access times to a first memory location 5 and to the second memory location 7 may differ. Since oftentimes the first memory location 5 or target memory 6 is a Flash-type memory and the second memory location 7 or the overlay memory 8 is a SRAM-type memory, the access times may differ due to the different access times due to different physical properties. This results in different read-out times of first and second memory locations 5, 7 from the memories 6, 8. Also the read-out time of the memories 6, 8 and of the first and second memory locations 5, 7 may differ due to contention when accessing a memory. For instance, multiple devices 1 may try to access one memory location 5, 7 or one memory 6, 8, meaning the same memory 6, 8 at a time, elongating the read-out time of the respective memory location 5, 7 or memory 6, 8. Also, contention may occur by multiple-access to a bus to which the memories 6, 8 are coupled.

The device 1 may contain a processor 1*a* processing the data from the target memory 5 or from the overlay memory 7 being read-out by the device 1. Since the data can, in most cases, be read-out by the device 1 or processor 1*a* quicker from the overlay memory 8 than from the target memory 6, the processor 1*a* may, in a conventional system, potentially process the read-out data earlier than it is supposed to do. This may lead to wrong data processing within the processor 1*a* since processing occurs too early. Ultimately, this may result in a complete failure, for example if some timing assumptions in the software may be violated. Alternatively, the software may run fine in a development mode, when a fast memory (for example the memory 8) is used, but fail in a real application scenario when a slower memory (for example the memory 6) is used, which would render the development mode unreliable.

Hence, the overlay mechanism 4 or the corresponding method for overlaying data may assign to each target address range a target access time. According to the disclosure the real time performance of the overlay system may be improved by modifying the timing behavior of the overlay system. This may work as follows: The target access time may describe the expected number of cycles required to perform an access or target access from the processor 1*a*. When an overlay translation is performed the actual number of cycles required to access the overlay memory 8 are counted. If the real number of cycles taken for the access (for example, of the overlay memory 8) is less than the target access time, the processor 1*a* is stalled by the difference in the number of cycles. This allows additional cycles to be added to the access time for the overlay memory 8 to give access time as would have been seen from the target memory 6. Hence, according to the disclosure the real time performance of the overlay system is improved by modifying the timing behavior of the overlay system. So according to the disclosure not only the problem of data table location is solved by also the problem of data access times. This is of interest since in a real-time system the access time of the data is critical. Real time consideration may be of interest since switching the data tables from (potentially slow) flash to (potentially fast) SRAM changes the real-time behavior of the system. This may cause unwanted effects.

So, in this manner it may be prevented that data being stored in the overlay memory 8 is read-out before (or faster than) data could be read-out in the target memory 6. In result, it is avoided that that the device 1 or the processor 1*a* receives and processes data before it is ready to read-out data. Also, the processor 1*a* may, for example, obtain data approximately with the same delay, irrespective of whether a development mode (memory overlay) is used or not. This means that in the signal path from the overlay memory 8 to a device 1 or to the processor 1*a* the overlay mechanism 4 prevents that the forwarding of data occurs before the device 1 or processor 1*a* is ready to do so (or faster than in a case in which the target memory is used). In reality, the overlay mechanism 4 may be part of the device 1 or of the processor 1*a*, or may partially be part of the device 1 or processor 1*a*. In that case the overlay mechanism 4 may—for example—prevent forwarding to that part of the device 1 or of the processor 1*a* doing the further processing. In other words, the hardware within the processor/device 1*a*, 1 or in the signal path even before the processors device 1*a*, 1 responsible for the overlaying of data may delay, or prevent for some time, a forwarding of data read-out from the overlay memory 8 to other parts of the processor 1*a* and/or the device 1 not involved in overlaying of data but doing regular computing or processing.

According to a potential modification, the delay of the overlay mechanism 4 of the devices 1 can be configured to compensate at least partially for a difference between access time of the first memory location 5 and the second memory location 7. Also the corresponding modification in the method comprises that the time of delaying access or the target access time is chosen to compensate at least partially an access time difference between accessing the first memory location 5 and accessing the second memory location 7.

By this feature, the difference in access times may be at least partially compensated. An access on data to the second memory location 7 by means of the overlaying mechanism 4 is delayed so that an access on the second memory location 7 is more likely to be completed when a direct access of the device 1 to the first memory location 5 would be completed. At least it may be achieved that the reduced access time on the second memory location 7 which might be a SRAM-type memory, compared to the access time of the first memory location 5, which might be a Flash type memory, is at least partially compensated. Due to this feature it may be attained that an access to a second memory location 7 via the overlay mechanism 4 is postponed or delayed for a certain time range or delay.

In a real-world scenario, the access time of the first memory location 5 may vary, so that a shorter access time to the first memory location 5 is possible, shorter than the mean access time to the first memory location 5. In other words, the access time to the first memory location 5 may be random in nature with a certain average. The more the input signal coming to the requesting device 1 or processor 1*a* via the overlay mechanism 4 or the overlay method is delayed to the mean access time of the first memory location 5, the more "realistic" access times are reached in the case of an overlay situation. Thus, the device 1 may be "ready" to deal or cope with that input. A device 1 or processor 1*a* may, for example, be considered ready to deal or cope with an input if an access time on a memory location 5, 7 has passed. Typically, an application software is running or cooperates with the device 1 or processor 1*a*. The access of the application software to the target memory 6 or the first memory location 5 is typically (or at least in some situations) random in nature. However, in general for random accesses on the second memory location 7, which may be a RAM or SRAM memory, a quicker access is possible than on the first memory location 5 or target memory 6, which may be Flash. So by this feature the stability of the processing operation may be enhanced as signal input from the second memory location 7 may occur more likely when the requesting device 1 or processor 1*a* can process the input signal or when the input signal would "normally" arrive (in the absence of an overlay). The access time may comprise signal propagation, basic logic operations and the time required to read out (physically) a memory location 5, 7.

In other words, by delaying the access time to the second memory location 7 by the overlay mechanism 4, it is attained that an input of data to the device 1 or partitions of the device 1 occurs, when the device 1 or partition of the device 1 is ready to deal with said input, or when said input would normally arrive in the absence of an overlay. So the real-time behavior of the system is not changed by overlaying data from the first memory location 5 to the second memory location 7, wherein typically the second memory location 7 allows a quicker access than the first memory location 5. For the above discussed reasons, in a real-time system the access time of the data is critical, and improvements can be achieved by adapting the access time in the case of memory location overlay when compared to a case without memory location overlay.

According to another aspect, the overlay mechanism 4 may be configured to redirect an access to a first target memory range 2 in the first memory location 5 to a first overlay memory range in the second memory location 7. Also the overlay mechanism 4 may redirect an access to a second target memory range to a second overlay memory range. The overlay mechanism 4 may be configured to apply a first delay in case of an access to the first target memory range and to apply a second delay, which is different from the first delay, in case of an access to the second target memory range in case of a redirection. By this modification, data accesses directed to the first or second target memory range may be redirected to a first or second overlay memory range of the second memory location 7.

The first or second overlay memory ranges, to which the data may be redirected, may have different access times. Also the first or second target memory range may have different access times. Typically to at least some degree the access times are random in nature. For instance this means the application software access to the target memories 6 may be typically random in nature. In general random accesses on SRAM are expected to be faster than on a Flash. The different access times may be considered by the overlay mechanism 4 and also by the corresponding method for overlaying data. Thus, the overlaying mechanism 4 may compensate the different access times. In other words, since the access time to each of the first and the second memory range may be adapted individually to the access time of the respective first and second target memory range, a specific adaption on expected access times is possible.

According to another aspect, the overlay mechanism 4 is configured to extend an access time to the second memory location 7 to be equal to or larger than a target access time in case of a redirection. By this modification it may be attained that an access time of a second memory location 7 takes at least a minimum time. In other words, the data arriving at the device 1 upon request (for example, a data read request) from the second memory location 7 are not processed by the device 1 or a processor 1*a* of the device 1 "too early", which would lead to a wrong processing or at least to a distortion of a real-time behavior (since, for example, an input signal with wrong data may be considered since the data arrive too early). This modification may especially be applied, if the respective data input to the processor is extremely critical. In other words, specifying a minimum delay may be useful to avoid in any case that the content or data in a memory location or range arrive too early at the processor 1*a* and thus, the processor 1*a* produces a false output, which may have severe consequences. In this context, "too early" means before a requested input from a first memory location or target memory 6 would be expected.

According to an aspect, an access time to the first memory location 5 may be longer than an undelayed access time to the second memory location 7. The target access time may be equal to or larger than the access time of the first memory location 5. Thereby, it is attained that an access to the second memory location 7 takes at least as long as an access time that would be expected if the device 1 intends to access the first memory location 1. Therefore, for the target access time a minimum time corresponding to the access time to the first memory location 5 may be defined. Thereby it may be ensured that a request by the processor 1*a*, which is redirected to the second memory location 7 and which may for example provide data previously processed or buffered by the overlay mechanism 4, may not be fulfilled or completed by the device 1 before corresponding data stored in the first memory location 5 would be available.

According to another aspect, the target access time may be programmable. This may be done by a user (or a user-provided software) defining a value in a user accessible register of the device 1. Thereby a user may specify this value such that real-time critical parameters, for instance when calibrating an engine by the device 1, may not be accessed by the device 1 (or by the processor 1*a*) earlier than expected. Also by this enhancement a security buffer in time may be considered when specifying the programmable target access time.

According to further aspect of the overlay mechanism 4, the overlay mechanism 4 may be configured to start or initialize an incrementing or decrementing counter in response to a detection that an overlay operation is performed. This is a possible realization of an additional delay that can be realized by stalling (or delaying) the point at which a "data valid" is seen at the processor Load-Store unit (or provided by the overlay mechanism). Also the overlay mechanism 4 may be configured to signal data received from the second memory location 7 as being available for a processor 1*a* in response to a detection that a predetermined number of clock cycles has elapsed since the starting or initializing of the counter. By using this concept, an easy implementation may be realized. In case of a decrementing counter, only when the counter is at zero the data may be seen as valid and available to the device 1 or the processor 1*a* to be further processed or forwarded in a processor pipeline. Also by using this enhancement a timing compensation between different memory accesses is realized.

If the overlay mechanism 4 is optionally extended to cover both code and data access, this overlay mechanism 4 may potentially be useful in compensating for timing differences associated with Flash-to-Flash overlay as required by various software-over-the-air (SOTA) implementations.

According to an optional enhancement, the target and overlay memory 6, 8 or the first and the second memory may be the same memory. In this case, the overlay mechanism 4 may be used to add additional delay cycles to every access from the memory. This may be used for tuning performance or power consumption.

Further, by using this enhancement, the overlay mechanism 4 may be employed within the area for duplication for locksteped implementations. This may support safe operation of the delay timer.

So by using the overlay mechanism 4 and the corresponding method as disclosed, a programmable delay is possible which allows to compensate for the timing difference between memory accesses 2, 3 to different memory ranges during data access overlay.

Figures 3, 4:
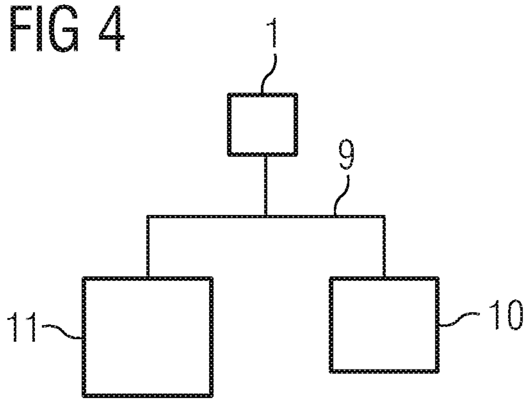
FIG. 3 illustrates schematically a third embodiment, wherein it is illustrated how an overlay access may be postponed by delaying or stalling some cycles.
FIG. 4 illustrates schematically a fourth embodiment and focuses how the interaction between a device and a first and a second memory location may interact via a bus.

In FIG. 3 an example of how overlaying works is illustrated using a table with different accessing and delaying or stalling times. In the left column, the different target memories 6 are specified. In this example the different memories are named Flash-1, Flash-2 or Flash 3. They may be a Flash-type memory, but in principle they could also be a SRAM-type or other memory type, like, for example, a ROM, a PROM, an EPROM, or the like. The three different memories or memory locations Flash-1, Flash-2 and Flash-3 may be physically in the same target memory 6 but they can also be in different target memories 6. In this example, the target memory 6 may correspond to the first memory location 5 but also the first memory location 5 may be a part or a range of the target memory 6. The Flash-1, the Flash-2 or the flash 3 may have different target access times. The target access times may be measured or described in terms of processing cycles of a processor 1*a* of the device 1 doing the overlaying or by the device 1 doing the overlaying, or on terms of bus cycles. In this illustrated example the Flash-1 has a target access time of 12 cycles (processor cycles or bus cycles), the Flash 2 has a target access time of 15 cycles and the Flash-3 has a target access time of 21 (measured in cycles). Since the first memory location 5 is at least part of the respective target memory 6, corresponding statements apply for the first memory location 5 and for the target memory 6 (sometimes also designated as "first memory location"). In other words, a first memory location designates a part of a target memory or a target memory in its entirety. Similarly, a second memory location may designate a part of the target memory mentioned before, or a part of another target memory, or the another target memory in its entirety.

During the overlaying, data (or a data access) is overlaid to a second memory location 7 (for example, by means of the mechanism 4 for overlaying data or by the method for overlaying data). The second memory location 7 is at least part of an overlay memory 8 but may also be the entire overlay memory 8. Different "second memory locations" 7 may also be in different overlay memories 8. This means the different overlay memories 8 may not be part of the same memory, for example within an integrated circuit (IC), or may be, for instance, even an external memory just connected by an interface to the IC on which the overlaying mechanism 4 takes place or the overlaying method is implemented.

An overlay access on a second memory location 7 which may be at least part of an overlay memory 8 also takes some time. The time may also be measured in processing cycles of a device 1 or a processor 1*a* doing the overlaying. In the illustrated table, the overlay access time for overlaying the second memory location 7 takes a different number of cycles for each "first memory location" 5 or target memory location Flash-1 Flash-2 and Flash-3. Namely access to target memory location Flash-1 takes 10 cycles, access to target memory location Flash-2 takes 14 cycles and access to target memory location Flash-3 takes 15 cycles. Apparently, in these examples, accessing the second memory location 7 (overlay access time) takes less cycles than accessing the first memory location 5 (target access time). Therefore the device 1 or the processor 1*a* doing the overlaying is delayed or stalled in order to compensate the time difference between accessing the first memory location 5 and the second memory location 7. The number of cycles being delayed (i.e. by which an access to the overlay memory is delayed or during which the processor is stalled) is the difference between the target access time and the overlay access time (both measured in cycles). In these examples the overlay access time on the Flash-1 (i.e. when the processor requests access to "Flash-1" and the access is overlaid or redirected to a "second memory location" corresponding to "Flash-1") is delayed (extended) by 2 cycles, the overlay access time on the Flash-2 is delayed for 1 cycle and the overlay access time on the Flash-3 is delayed for 6 cycles. By delaying for the said number of cycles an access on the respective second memory location, the access is delayed so much that it occurs with a same timing (or even afterwards) when compared to an access directed directly to the first memory location 5 (target access time). In this way, an access of the device 1 or of the processor 1*a* requesting data from the first memory location 5, which is overlaid to the second memory location 7, is not possible (or completed) until an access on the first memory location 5 would be possible (or completed). Therefore it is avoided that the processor 1*a* or the device processes wrong data and thus, in consequence may produce the wrong output.

But in reality also a second scenario is possible (as illustrated in the lower block in FIG. 3). The lower block in FIG. 3 illustrates an example of a "Flash-1" first memory location 5. In this case, the target access time on the first memory location 5 still takes 12 cycles. But in contrast to the access on the "Flash-1" memory in the previously discussed example, now the overlay access time on the second memory location 7 (which is the overlay memory for "Flash-1") takes 15 cycles. Apparently, now it takes longer to access the second memory location 7 in the overlay memory 8 than the processor expects for an access of data stored in the corresponding first memory location 5. The difference between the number of cycles when accessing the first memory location 5 and the second (overlay) memory location 7 is now 3 but the sign is negative. In that case, the device 1 or the processor 1*a* is delayed or stalled for 0 cycles, as accessing the second memory location 7 (overlay access time) takes longer than accessing the first memory location 5 (target access time). This is not a problem since even if the overlay access time is longer than the target access time it is ensured that data is not processed by the processor 1*a* or the device 1 too early. In this example the algorithm running on the device 1 or processor 1*a* is typically implemented to cope with an input arriving somewhat later than typically expected from the first memory location 5. So there is no problem for the overlaying method or the overlay mechanism.

Such a scenario is likely to occur if many accesses on the same second memory location occur at the same time. In this case an access time to the second memory location 7 increases significantly, so that an access is likely to take longer than an access to a first memory location 5. Also such a scenario is likely to occur if the signal path is long or comprises many obstacles taking time to be passed by a signal. Such an obstacle may be for example a number or bridges on a bus causing a long delay. Such a long delay may be 5, 10, 15, 25 or more processor cycles.

So, in other words, the overlay memory 8 is not always faster than the target memory 6. This depends on where in the system the target memory 6 and the overlay memory 8 are relative to the requesting processor 1*a* and also on the contention of the target memory 6, the bus system and the overlay memory 8. The application software access to the target memories 6 is typically random in nature. In general, for random accesses SRAM is expected to be faster than a Flash. In case where the target access time is less than the overlay access time no additional delay is added.

In FIG. 4 an entire system for overlaying is illustrated. By means of a device 1 an overlay mechanism 4 or a method for overlaying data may be performed. In FIG. 4 a device 1 connects a first memory location 10 and a second memory location 11 via bus 9. Thereby both memory locations 10, 11 are connected via the same bus 9. The device 1 comprises an overlay mechanism 4 which it configured to or configurable to redirect an access which is directed to the first memory location 10 to a second memory location 11. Therefore data which is intended by the processor 1*a* in the device 1 or the device 1 (or by the respective software) to be stored in a first memory location 10 is stored in a second memory location 11 instead. So it may be avoided to wear-out the first memory location 10, since the information is stored instead in the second memory location 11. The access time of data being stored in the second memory location 11 might differ from the access time of data being stored in the first memory location 10.

In other words, rather than re-writing the flash-memory (for example, the first memory location 10) at every data table change, the data values may be placed in a SRAM (for example, at the second memory location 11). Rewriting a flash may be time consuming and may lead to a flash wear-out. Typically the first memory location 10 may be implemented as a flash and the second memory location may be implemented as a SRAM.

In FIG. 4 the delay is added on the side of the device 1 of the bus 9. It is better to add the delay there than (centrally) at the overlay memory 8, which may comprise the second memory location 11. This is since the overlay memory 8 has no idea of how far away the requesting processor is in the system or which target 6 (which may comprise the first memory location 10) it is overlaying so it can only provide an "average" delay unless a complex delay system was incooperated. This would require additional information being provided over the bus 9 to identify the overlay operation being performed.

Providing the mechanism (for example, the overlay mechanism described herein) at the processor 1 allows re-use of current overlay logic. In principle about any SRAM may be used in the system as an overlay memory 8 (DSPR, PSPR, LMU, DLUM, EMEM). Implementing the delay logic (within the overlay mechanism 4) at the requesting node (processor 1*a*) rather than at the SRAM (overlay memory 8 or second memory location 11) leads to a simpler system.

The access time on the second memory location 11 may be reduced. This may be caused by a lower number of contentions on the second memory location 11 than on the first memory location 10. For instance if one device 1 in the system often requests data from the same first memory (comprising, for example, memory location 10) it may have a significantly increased response or access time. In principle, the same applies (speaking of contentions) to any other memory, other than the memory comprising the first memory location 10, including the memory comprising the second memory location 11.

Also the first and the second memory location 10, 11 may be a different type of memory. For instance, the first memory location 5, 11 is a flash-type and the second memory location 7, 11 is a SRAM type. Hence, the access time due to the different physical properties may also be different since a flash-type memory has a shorter access time than an SRAM-type memory.

According to a further aspect, the overlay mechanism 4 can be configured to adapt the delay depending on (known or estimated) access times of memory locations 10, 11. The overlay mechanism 4 and/or the corresponding method may detect if a second access to the first memory location 10 follows (for example, in terms of a memory address to be accessed) on a first access to the first memory location 10, causing a changed access time to the first memory location 10 when accessing successional memory locations of the first memory location 10. This may result in the changed access time being shorter than the time of the first access to the first memory location 10. In this case the delay (applied when performing memory overlaying) can be adapted to the changed access time of the first memory location 10 when accessing the second memory location 11. So the shorter access time when accessing the second time (in succession) may be compensated.

In many real scenarios, a device 1 which may comprise a processor 1*a* may request for data being successional (for example, at directly subsequent memory locations), concatenated or associated in a memory location 10, 11. Therefore, in such a scenario, successional, concatenated or associated memory locations within a memory 10, 11 can be accessed quicker by the device 1 (for example, starting from the second access on the memory location 10, 11 of a sequence of successional accesses).

For instance associated, concatenated or successional memory locations 5, 7 may by loaded into a prefetch buffer of the first memory location 5 in response to a first access on the memory location, thus allowing quicker access on the data stored in the prefetch memory. The device 1 may be aware of this changed access time. The changed access time (for the second and further successional accesses) is typically shorter than the access time for the first time access to the memory location. Therefore, the program running in the device 1 or in the processor 1*a* can expect an input earlier if an associated, concatenated or successional memory location 10, 11 is accessed by the device 1 or by the processor 1*a*. So the delay of the overlay mechanism 4 and of the corresponding method may be adapted to the earlier input. The delay of the overlay mechanism 4 may elongate the access time to the second memory location 11 to the access time of the first memory location 10 or may add a delay to the access time to the second memory so that the delay and the access time to the second memory 11 together are a longer time than the access time on the first memory location 10.

According to an aspect, the device 1 may be connectable or may be connected to the first and second memory location 10, 11 by at least one bus 9. By means of a bus 9, a communication in a defined, known or predictable manner is possible since a bus may provide a well-tested exchange of signals or data. However, some uncertainties of the access time may also arise, for example in the case of contention.

According to another aspect, the overlay mechanism 4 may be configured to compensate for varying un-delayed access times to the second memory location 7. When accessing a real memory (for example, the second memory location), the required time may vary statistically. An overlay mechanism 4 according to this modification may compensate such statistical varying access times to the second memory location 7.

The embodiment illustrated in FIG. 4 can be combined with the device illustrated in FIG. 1. In that case, the accesses directed to the first memory location 2 and the accesses directed to the second memory location 3 shown in FIG. 1 employ both the (same) bus 9 in FIG. 4 in order to access the first and second memory locations 10, 11. In other words, memory location 10 corresponds to memory location 2, and memory location 11 corresponds to memory location 3.

Also, the embodiment illustrated in FIG. 4 can be combined with the embodiment illustrated in FIG. 2. In that case the bus 9 corresponds to the data access (line) 19. The first memory location 10 corresponds to a section of the target memory 6 or to the entire target memory 6 and the second memory location 11 corresponds to a section of the overlay memory 8 or to the entire overlay memory 8. The section of the target memory 6 may be equal to the first memory location 5 in FIG. 2. The section of the overlay memory 8 may be equal to the second memory location 7 in FIG. 2.

Figure 5:
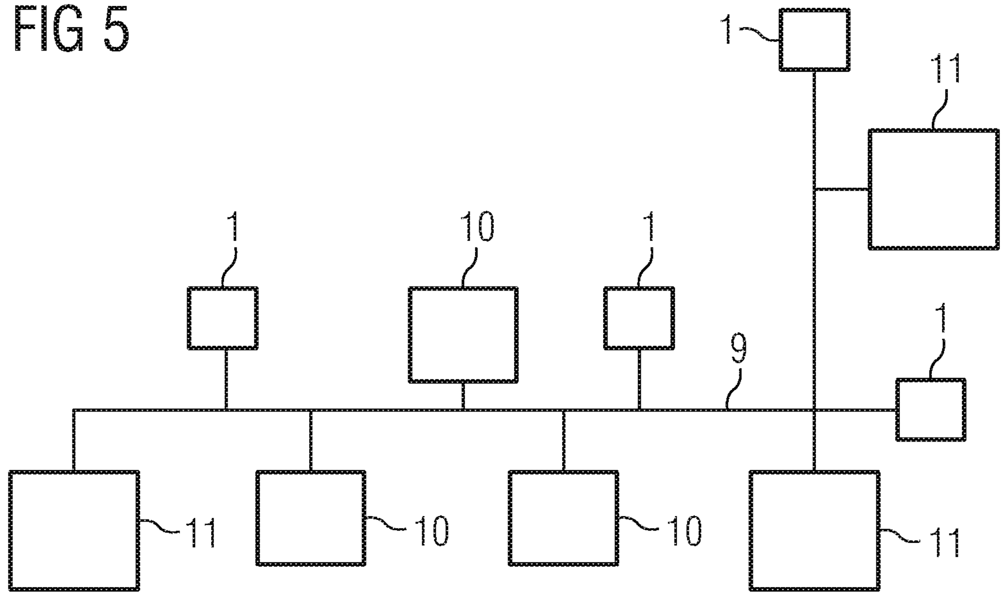
FIG. 5 illustrates a fifth embodiment being an enhanced version of the embodiment illustrated in FIG. 4 having multiple actors of at least one of a device, a first type memory location and a second type memory location.

In FIG. 5, a further embodiment is illustrated. In principle it comprises the same components as already described in FIG. 4, for instance, a device 1, a bus 9, a first memory location 10 and a second memory location 11. Accordingly, reference is made to the description of these components and their interaction in FIG. 4. The details regarding the interaction of the components as described when discussing a combination of FIG. 1 and FIG. 4 or FIGS. 2 and 4 also apply.

In FIG. 5 it is illustrated that more than one of one instance of components 1, 10, 11 may be employed and that multiple components may rely on one (shared) bus 9. For instance several (for example, between 2 and 10) devices 1 rely on one bus 9. Also in principle several (for instance between 2 and 10) first memory locations 10 and/or second memory locations 11, may access or employ one bus 9. So, a typical system may contain or comprise multiple processors 1*a*, multiple flash memories and/or multiple overlay memories, which may, for example, be coupled via one bus, or via different segments of a bus. Using this mechanisms, each processor's overlay operation may be separately adjusted for its view of the flash and overlay memory access times. According to the disclosure, different target access times are allowed to be defined for each target range and hence for each flash memory. The first memory locations 10 may, be but do not have to be, of one given type of memory. For example, a flash type memory may be used for the first memory locations 10. Also the second memory locations 11 may be, but do not have to be, of one given type of memory. Nevertheless, a SRAM-type memory may be used for the second memory locations 11. In principle the first memory location 10 and the second memory location 11 might be a SRAM-type or a Flash-type memory.

In principle, also one memory (which may be a SRAM-type or flash-type memory) may serve jointly as a first memory location 10 and a second memory location 11. In this case different sections or ranges of the memory serve for different purposes, one as a first memory location and the other one as a second memory location. However, it is preferred that the first memory location(s) and the second memory location(s) use different types of memory (having different access times).

In such an embodiment as illustrated in FIG. 5 contentions when accessing a memory location 10, 11 or memory 6, 8 are likely to occur. This is due to the multiple number of "actors", especially devices 1, all requesting data from memory locations 10, 11. This may occur (almost) jointly, meaning almost in a time-parallel manner. Therefore a human user programming the algorithms or programs running on a device 1 can estimate—due to his experience and due to his knowledge of the topology of the bus 9 and of the actors—how long an expected access time on a first memory location 10 is likely to be. Therefore a human user can provide to the overlaying mechanism 4 or to the method for overlaying data an input (for example, by inserting a configuration instruction into a software portion) how long it takes for a certain device 1 (incorporating or cooperating with an overlay mechanism 4) to access a first memory location 10. Also, a user may chose for security critical applications an expected access time to be so long that the device 1 can access the first memory location 10 in any case, for example with a probability higher than 99% or 99, 9%. Therefore, it is ensured or guaranteed that the device does not operate faster in the case of a memory overlaying when compared to an operation without a memory overlaying. This is due to the long access time for the overlaying situation which may be specified by the user. The access time for the overlaying situation may be defined by the programmable delay.

However, within the scope of this disclosure the access time could also be fix-programmed (unchangeable by a user). In that case, it may be specified by the device manufacturer how long it typically takes for accessing the first memory location 10. This may be suitable if a person skilled working with such system does not have enough knowledge about the access times to be expected.

A third option would be that a default access time for accessing the first memory location 10 is programmed. This default value may be changed by a user for special purposes. Such a default access time may be useful in order to ensure a working system without too many modifications in an early testing stage, for example when calibrating an engine (or when designing and fine-tuning an engine control software). In case later on during calibration more specific knowledge is available and also more resources are available to consider details during calibration (fine-tuning), the default access time of a first memory location 10 may be adapted.

According to this disclosure it is also possible to mix the three different options for different parameters or data, which may be intended by the device 1 to be stored on the first memory location 10.

In principle according to this disclosure such features are also possible for the embodiments illustrated in FIG. 4. Nevertheless they will rather be applied in a system with multiple components 1, 10, 11, as in such a system access times are more complicated to determine.

Figure 6:
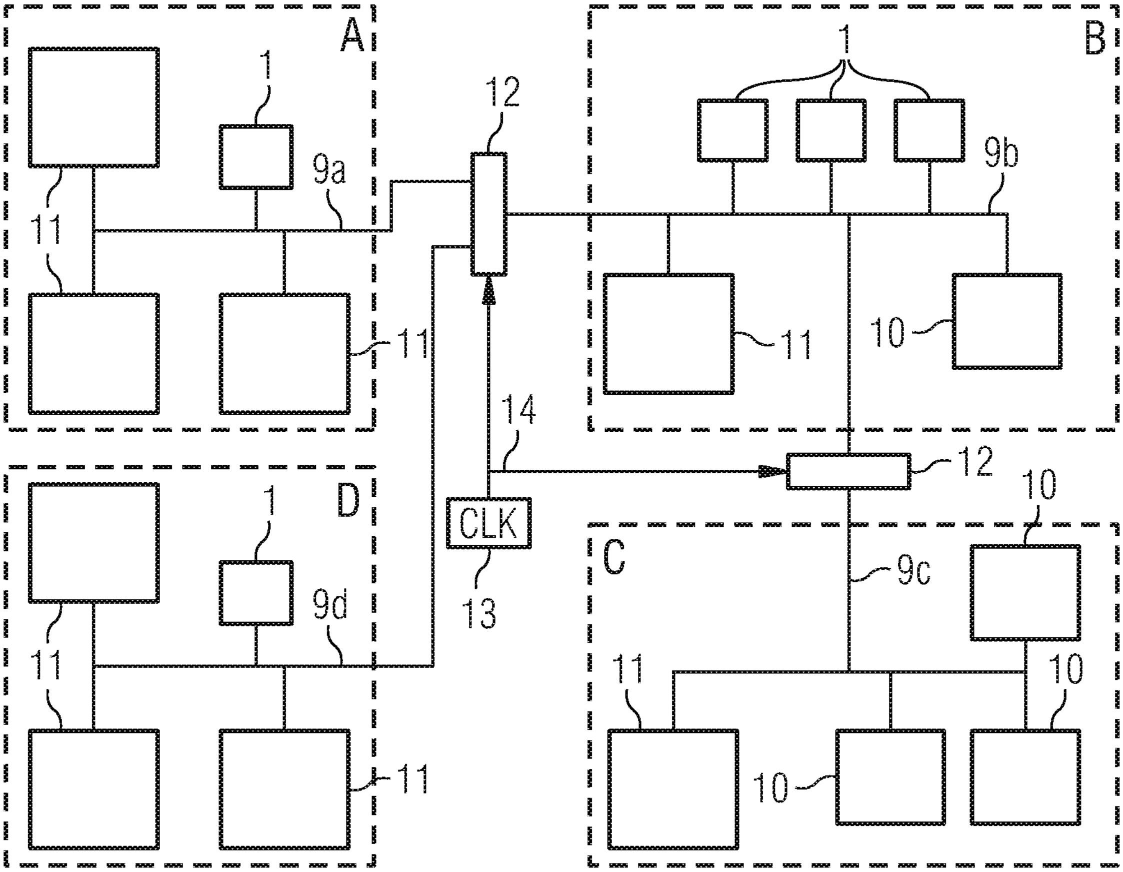
FIG. 6 illustrates a sixth embodiment being an enhanced version of the embodiment illustrated in FIG. 4 or 5, to illustrate how multiple busses or bus segments may interact by means of at least one bridge forming the interface between at least two bus segments or busses to be connected.

FIG. 6 illustrates a further embodiment teaching a system with different segments **9*a*, 9*b*, 9*c*, 9*d* of the bus 9. The segments of the bus 9*a*-9*d* each comprise one or more bus lines. The bus lines may be uninterrupted within one segment 9*a*-9*d*. The different segments are (partially) connected to each other by at least one bridge 12. In the example, the bus segments 9*a*, 9*b*, 9*d* are connected by one bridge 12. The bus segments 9*a*, 9*b*, 9*c* are connected in series by two bridges 12. The bus segments 9*a*, 9*b*, 9*c* are electrically connected as enumerated. In principle (although not illustrated) a circular-design of bus segments 9*a*-9*d* is also possible within this disclosure. The bridges 12 may, for example, be clocked by a common clock signal 14 originating from a common clock 13. In summary the bridges 12 may serve for an exchange of signals or data between bus segments 9*a*-9*d* and may also serve for a (time-) synchronization of bus segments 9*a*-9*d*. Nevertheless the bridges 12 cause an unintentional delay which may contribute significantly to the transmission time over the bus 9, meaning from one component 1, 10, 11 in a first bus segment 9*a*-9*d* to a second component 1, 10, 11 in a different bus segment 9*a*-9*d***.

A bus segment **9*a*-9*d* may comprise (or may be directly coupled with) at least one of a device 1, a first memory location 10 and a second memory location 11. For instance, the illustrated bus segment 9*a* accesses (or connects) a device 1, and three different first memory locations 11. The bus segment 9*b* accesses or connects three devices 1, one first memory location 10 and a second memory location 11. The bus segment 9*c* accesses or connects exclusively first and second memory locations 10, 11 but does not comprise a device 1. Thus, in case the memory locations in segment C or bus segment 9*c* are accessed, this can only occur by devices 1 being in other bus segments 9*a*, 9*b*, 9*d*. The illustrated bus segment 9*d* comprises a device 1 and three second memory locations 11. In principle a device 1 in a first bus segment 9*a*-9*d* can also access memory locations 10, 11 in other bus segments 9*a*-9*d*. This may depend on availability of memory resources or may make sense for duplication of data storage. For instance in case one segment A-D is damaged (for example by ESD or semiconductor degeneration over time), data may be stored in other segments A-D. This may especially apply if one segment A-D is an external segment. External means, in this context, not being a bus segment being part of one chip but being externally connected by an interface (which may comprise a bridge 12) to the chip comprising at least some of the other segments A-D or bus segments 9*a*-9*d***.

The "signal delay by purpose" (which is applied in the case of an overlaying operation) occurs on the side of the device 1, not on the side of the memory location 10, 11 being the overlay memory 8 to which a data access is redirected. Indeed, it is applied by the overlaying mechanism 4 of the device 1. The second memory location 11 (or the overlay memory 8) has no idea (does not possess the information) of how far away the requesting device 1 or processors **1*a* is in the system or which first memory location 10 or target location or target memory 6 it is overlaying. So, if there was a delay being implemented on the side of the second memory location 11 or on the side of the overlay memory 8, only an average delay or another (common) delay, for example being the maximum expectable delay, could be used easily (without additional signaling efforts). This problem could only be circumvented by a complex delay system if a delay at the side of the memory was used. Such a complex delay system would possibly provide the information about the delay the device 1 or processor expects for a respective first memory location 10 or a target memory 6 to the second memory location 11 or the overlay memory 8. In that case, the second memory location 11 or the overlay memory would be able to perform the delaying of access to the second memory location 11 or overlay memory 8 by a respective processor 1*a* or device 1**.

Providing the overlay mechanism 4 or delay mechanism at the processor **1*a* or at the device 1** (or at least at the side of that components) allows the re-use of the (current)

overlay logic. In principle for instance for an overlay memory 8 or a second memory location 11 any SRAM in the system may be employed. This system comprises different memory regions or memory types, for example designated as DSPR, PSPR, LMU, DLMU and/or EMEM in some embodiments. Implementing the delay logic at the processor 1*a* or at the device 1 (generally speaking at the requesting node) rather than at the overlay memory 8 or at the second memory location 11 (possibly a SRAM) may lead to a far simpler system.

The previously discussed system may optionally comprise additional possible features, modifications or enhancements.

In an embodiment, the bus segments 9*a*-9*d* may be coupled via one or more bridges 12. The memories 10, 11 may be coupled with different segments 9*a*-9*d* of the bus structure 9. A first device 1 or a first processor 1*a* and a second device 1 or a second processor 1*a* may be coupled with different segments 9*a*-9*d* of the bus structure 9. The memories 10, 11 may comprise target memory ranges (which may, for example, be used during a "normal" program execution) and overlay memory ranges (which may, for example, be used during a program development or program tuning operation). A relationship between an access time of the first processor 1*a* to a target memory range associated with an operation of the first processor 1*a* and an undelayed access time of the first processor 1*a* to an overlay memory range associated with the operation of the first processor may be different from a relationship between an access time of the second processor to a target memory range associated with an operation of the second processor and an undelayed access time of the second processor to an overlay memory range associated with the operation of the second processor. A delay of the overlay mechanism 4 of the first device and a delay of the overlay mechanism 4 of the second device may be programmable individually and may allow a compensation of the different relationships between access times to target memory ranges and corresponding overlay memory ranges.

By this feature a user or human user who knows the system architecture and system characteristics can react on requirements by specifying individual delays for different processors or different delay for the first and the second processor (for example, using configuration instructions included in a code). For instance, the number of bridges 12 in the signal path over the bus 9 between a first or second device 1, which may comprise a processor 1*a*, and at least one of a first and second memory location 5, 7 may differ. Since a bridge 12 has a significant effect on signal delay or signal propagation time on bus 9, the number of bridges 12 in the signal path influences the access time of a device 1 including an overlay mechanism 4. Also, a user may estimate the number of signal contentions from the view of a device 1. For instance, a user may consider that a device 1 may access a memory location 10, 11, while one or more of the other devices 1 may access one other memory location 10, 11. In such a scenario, the one or more other devices 1 accessing the other memory location 10, 11 may cause some bus contention when accessing the memory locations 10, 11. Therefore, when programming a delay for the overlay mechanism 4, the user may program a longer delay time since a long access time may be expected when the device 1 may intend to access the first memory location 10. This may be caused by either or both the number of bridges 12 in the pathway or the contentions expected when accessing the memory location 10, 11.

In other words, an actual difference (or actual average distance, or estimated actual difference) between access times to a target memory range and to an overlay memory range may be considered by a user when programming a delay for the overlay mechanism. One delay component may be determined by the architecture of the bus system or bus systems, wherein a number of bridges between a given processor and a physical memory comprising the target memory range may be different from a number of bridges between the given processor and a physical memory comprising the overlay memory range. Furthermore, contention-based delays may be different for an access to the target memory range and for an access to the overlay memory range. Thus, the delay for the overlay mechanism may be programmed individually on the basis of a knowledge of the location of the respective processor within a bus system, a knowledge of the physical memories involved within the bus system, and an known or estimated delay impact caused by bus contention or other factors.

Thus, by using such a system comprising a bus system with bus segments 9*a*-9*d*, an individual access time of a device 1 to a second memory location 11 (and also to a first memory location) can be taken into consideration. The access time of devices 1 to the second memory location 11 may differ, since, for instance, the signal path from a first device 1 to a corresponding second memory location 11 may differ from a signal path from a second device 1 to a corresponding second memory location 11. For instance there may be a different number of bridges 12 in the signal path of a bus 9 or bus system, or the access time from a device 1 to a corresponding second memory location 11 may differ from the access time from another device 1 to a corresponding (other) second memory location 11 since there are a different number of contentions on the signal path to be considered. For instance, when the first device 1 in segment A accesses a (corresponding) second memory location in segment C, two bridges 11 have to be passed since the only way is crossing segment B. In contrast, an access of device 1 in segment B is not delayed by the bus architecture when accessing a first or second memory location 10, 11 in segment B. However, when a device 1 in segment B is trying to access a second memory location 10, 11 in segment C, the access is delayed by one bridge 12. So, the access time for a device 1 to a first or second memory 10, 11 depends on the one hand on the signal path and on the other hand on the number of contentions on the bus 9 when accessing a memory 10, 11 location. Also the physical type of the memory location 10, 11 contributes to the access time.

So, the access time of an overlay memory 8 (which may by a second memory location 11) as seen from the processor 1*a* (which may be part of a device 1) may not be a constant due to contention at the bus system 9 and the overlay memory 8. The use of a variable delay on the returning data provides a degree of compensation for this contention. Thereby returning data may be the data being requested by the processor 1*a* or device 1 in the bus system 9. The returning data may be stored in the overlay memory 8 or the second memory location 11.

Figure 7A:
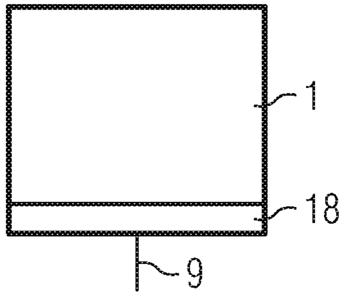
FIGS. 7*a* and 7*b* illustrate a device and the interface of the device to a bus according to a 7th embodiment, wherein there is a delay unit within the device (FIG. 7*a*) or at the interface between the bus and the device (FIG. 7*b*)
Figure 7B:
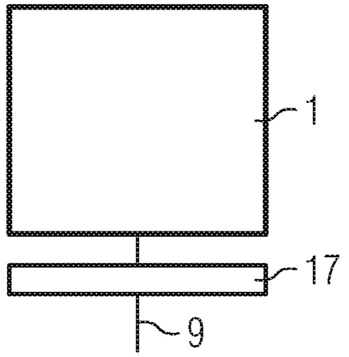

In FIG. 7 two different options are illustrated how the delay might work. In FIG. 7*a*, there is an internal delay unit 18 being part of the device 1 performing the overlay mechanism 4. Before an input signal (which may be a response of a memory read request) is allowed to pass from the bus 9 to a processor core, it is delayed by a delay unit 18. The bus 9 may also be a bus segment 9*a*-9*d* as discussed in FIG. 6. In other words, parts of the device 1 may function as an overlay mechanism 4 which comprises a delay unit 18.

This may be implemented within a processor 1*a* being part of the device 1 (or forming the device). In that case the delay by the delay unit 18 may be realized by skipping or stalling some cycles of the processor 1*a* before the signal coming in from the bus 9 is forwarded to further part of the processor 1*a* not being involved in the delay (for example, to a processor core). In this implementation the delay unit 18 is also part of the processor 1*a*.

According to another option, there is an external delay unit 17 as illustrated in FIG. 7 *b*). This means the delay unit 17 is not part of the device 1 but forms an interface between the device 1 and the bus 9 or bus segment 9*a*-9*d*. In other words, the device 1 comprises an overlay mechanism 4 configured to or being configurable to redirect and delay access to a second memory location 3. For example, the delay unit may delay the data read from the overlay memory location, and/or a "data ready" signal.

The overlay mechanism 4 outputs to the delay unit 17 an information describing by how much a requested signal (for example read data) from the second memory location 11 is to be delayed. The "signal" typically comprises data which was stored in the second memory location 11.

In an example, a delay to be applied by the delay unit may be programmable. For example, the processor may write a delay value to a "special function register" (for example, using one or more program instructions), and the delay value stored in said special function register may determine the delay to be used by the delay unit.

Alternatively the delay unit 17 might, for example, obtain a delay information or a delay value from the device 1, which is specified by the device 1 in a fixed manner or which is specified by default within the device 1. In contrast to the solution in FIG. 7 *a*) an additional component, namely the delay unit 17, may form an interface. Nevertheless, in this case, the device 1 does not need to provide resources as, for example, processing time or hardware resources, for the delay.

According to another aspect, the device 1 may comprise a processor 1*a*. The method for overlaying data or the overlay mechanism 4 may delay a processing operation of the processor 1*a* requesting access to the first memory location 10 or may delay a forwarding of data from the bus 9 to the processor 1*a*, to thereby delay access to the second memory location 11.

The processor 1*a* in the device 1 may request for data being stored in a first memory location 10. Since the access to data being stored in the first memory location 10 may be redirected by the overlay mechanism 4 to the second memory location 11, the access (or the effective access time) of the processor 1*a* to the second memory location 11 needs to be prolonged before the data is further processed in the processor 1*a*, which is attained by this modification. According to the a first option of this modification, this may be realized by delaying a processing operation of the processor 1*a*. For example by internal slow-down or halting of the processor 1*a* itself, a prolongation of access time on the second memory location 11 is attained. The first option may be implemented by an overlay mechanism or a method for overlaying data which may be delaying a processing operation by stalling at least one cycle of the processor 1*a*. According to this option, the delay may be achieved by the processor 1*a* itself. In other words, parts of the processor 1*a* or device 1 work as a delay unit 18. This may be possible without other functional units coupled to the processor 1*a* or overlay mechanism 4 for the purpose of delaying.

According to the second option of this modification, a delay may be realized by delaying a forwarding of data from the bus 9 to the processor 1*a*. This may occur by means of a delay unit 17 which may be at an interface of the bus 9 and the processor 1*a*.

In principle both devices 1 and delay units 17, 18 as illustrated in FIG. 7 can be combined with any other aspects and embodiments being discussed in this disclosure.

Figure 8:
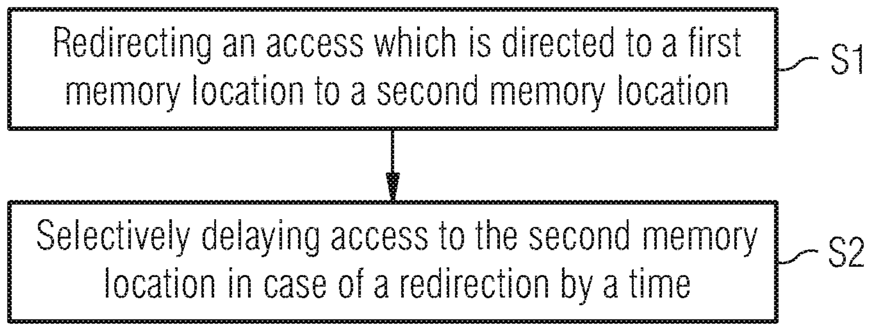
FIG. 8 shows a flow chart of an embodiment illustrating a method how overlaying data works including a subsequent access on second memory location.

FIG. 8 illustrates a flow chart how an overlay mechanism 4 or a method for overlaying data according to an embodiment may, for example, work.

There are two steps illustrated: In the first step S1, an access which is directed to a first memory location 10 is redirected to a second memory location 11. The second step S2 involves a selective delaying of an access to the second memory location 11 in case of a redirection by a time.

In the first step S1, data is stored in a second memory location 11. This may be done by the overlaying mechanism 4 being part of the device 1, as discussed previously. Therefore data which is intended to be stored by the device 1 or processor 1*a* in a first memory location 10 is stored in the second memory location 11 instead. So a wearing-out of the first memory location 11 is prolonged. Since the first memory location 10 oftentimes has a longer access time than the second memory location 11, data being stored in the second memory location 11 instead of the first memory location 10 can be accessed quicker. In some cases, the device 1 requesting for a data access to the first memory location 10 (which is redirected by the overlay mechanism 4 or method to the second memory location 11) is not ready to process such an input signal or might produce a wrong output since the input signal is processed too early, or a result of the processing may not represent a "real world" result which would be obtained without a redirection. Therefore an access to the second memory location 11 is delayed selectively (step S2) in case of a redirection, in order to avoid this problem. This occurs within the device 1 or in the signal path from the second memory location 11 to the device 1 directly before the device 1.

According to the disclosure all the aspects, embodiments, features or the like can be combined. According to the disclosure, all components, comprising the devices 1, processors 1*a*, busses 9, bus segments 9*a*-9*d*, bridges 12, first memory locations 10, second memory locations 11, target memories 6 and/or overlay memories 8 may be on one single chip. Nevertheless they may also be on different chips. Also the chip might include at least the processor 1*a* or device 1 and other components, but at least one of the memories 6, 8 or memory locations 10, 11 might be external. This may be especially suitable for data duplication.

CONCLUSIONS

The disclosure refers to an overlay mechanism or method redirecting data load access from a first memory location to a second memory location. Such a mechanism called data access overlay can be used by a customer during product development stage. Such a mechanism can be employed when calibrating an engine management system. In such a calibration system a data table that resides in the flash memory can be tuned. This may involve frequent modification to the table values. A first memory possibly may be a flash memory and a second memory may be a SRAM memory. Rewriting the flash memory at every data table change is time consuming and may lead to a wear-out of the first memory, which applies especially if the first memory is a flash-type memory. The change in location of the data is not visible to the application software but may be performed by hardware within a device or processor under control of the debug/calibration system. The hardware may contain a programmable table of target address ranges and an associated set of redirect address ranges to be substituted if a data access is performed to the target address range. The redirect address ranges are SRAM locations and may be any SRAM in a system comprising DSPR, PSPR, LMU, EMEM.

The disclosure discusses a device, comprising an overlay mechanism configured or configurable to redirect an access which is directed to a first memory location to a second memory location. The overlay mechanism is configured or configurable to delay access to the second memory location in the case of a redirection.

By such an overlay mechanism it can be attained that a device employs a second memory location instead of a first memory location. Since the first memory location needs not to be employed a wear-out of the first memory location can be avoided. Since due to the overlay mechanism the second memory location can be employed instead of the first memory location, the second memory location can be accessed more quickly from the device than the first memory location. In other words, the content of the second memory location can be read-out more quickly. Therefore the access to the second memory location may be delayed in order to compensate this.

Also the disclosure discusses a method for overlaying data. The method comprises redirecting an access which is directed to a first memory location to a second memory location, and selectively delaying access to the second memory location in case of a redirection by a time. Delaying means in the context of this disclosure an intentional delaying during signal or data processing or that a delaying or postponing of signal processing occurs by purpose. In other words, the delay according to this disclosure is different to a parasitic delay which may occur in signal processing in a device, system or chip unintentionally due to side effects of some components. Such a side-effect may by a response time of a circuit consisting for instance of transistors like MOSFETs, bipolar transistors and capacities or the like.

In principle the method provides the same advantages as the device. Since an access occurs to data being stored in a second memory location, the data can be accessed more quickly than data being in the first memory location. Therefore by the overlay method, which selectively delays access to the second memory location in case of a redirection by a time, the access to the second memory location by the device requesting access may be delayed or postponed.

Also the disclosure discusses a system comprising a first device as already mentioned, wherein the first device comprises a first processor; a second device as already mentioned, wherein the second device comprises a second processor; a bus structure comprising a plurality of bus segments;

and a plurality of memories. The first processor and the second processor are coupled with the memories via the bus structure. A delay of the overlay mechanism of the first device and a delay of the overlay mechanism of the second device are programmable individually.

In a device or system design numerous modifications, aspects and features are possible comprising for instance following features and modifications. Also corresponding features and modifications for the method are possible.

By all of the aspects, features or the like discussed so far an overlaying of a second memory location or a flash memory may be possible without impacting a time or real-time behavior of the device or a system comprising the device is possible.

To further conclude, some embodiments provide a mechanism to redirect data load accesses from flash memory to SRAM memory. This mechanism is known as data access overlay and is typically used by a customer during the product development stage when they are calibrating, for example, the engine management systems. In such a calibration system, data tables that reside in the flash memory are being “tuned”. This sometimes involves frequent modification to the table values. Rather than re-write the flash memory at every data table change (which is time consuming and leads to flash wear-out), the data values are placed in SRAM. The change in location of the data is not visible to the application software but is performed by hardware within the processor under control of the debug/calibration system. This hardware contains a programmable table of target address ranges and an associated set of redirect address ranges to be substituted if a data access is performed to the target address range. The redirect address ranges are SRAM locations and may be any SRAM in the system (DSPR, PSPR, LMU, EMEM).

This system allows the logical translation of addresses without modification of the application software and hence allows the Flash data tables to be “overlayed” by the SRAM. This solution solves the problem of data table location. However, embodiments according to the disclosure also address the problem of data access times. In a real time system the access time of the data is critical. It has been found that switching the data tables from (slow) flash to (fast) SRAM should not changes the real-time behavior of the system.

Embodiments seek to improve the real time performance of the overlay system by modifying the timing behavior of the overlay system described above. The proposed operation is as follows:

Each target address range is assigned a target access time describing the expected number of cycles required to perform an access to the memory from the processor. When an overlay translation is performed the actual number of cycles required to access the overlay memory are counted. If the real number of cycles taken for the access is less than the target access time the processor is stalled by the difference in the number of cycles. This allows additional cycles to be added to the access time for the overlay memory to give the same access time as would have been seen from the target memory.

It should be noted that the access time of the overlay memory as seen from a processor will sometimes not be a constant due to contention at the bus system and overlay memory. The use of a variable delay on the returning data provides a degree of compensation for this contention.

A typical system contains multiple processors, multiple flash memories and may contain multiple overlay memories. Using this mechanism each processors overlay operation may be separately adjusted for its view of the flash and overlay memory access times. This proposal allows different target access times to be defined for each target range and hence for each flash memory.

The proposed system is better than adding delay centrally at the Overlay memory. The Overlay memory has no idea of how far way the requesting processor is in the system or which target it is overlaying so can only provide an “average” delay unless a complex delay system is incorporated. This would require additional information being provided over the bus to identify the overlay operation being performed. Providing the mechanism at the processor (as proposed herein) allows re-use of the current overlay logic. We can use just about any SRAM in the system as an overlay memory (for example, DSPR, PSPR, LMU, DLMU, EMEM).

Implementing the delay logic at the requesting node (in or close to the processor requesting to read data) rather than the SRAM leads to a far simpler system.

It should be noted that the Overlay memory is not always faster than the Target memory.

Rather, this will depend on where in the system the target memory and the overlay memory are relative to the requesting processor and also on the contention at the target memory, the bus system and the overlay memory. The application software access to the target memories is typically random in nature. In general for random accesses we expect SRAM to be faster than Flash. In the case where the target access time is less than the overlay access time no additional delay is added.

The additional delay can be easily added by stalling the point at which data valid is seen at the processor Load-Store unit. The easiest implementation of the delay counter and delay operation would be to load a decrementing counter with the target access time when an overlay operation is detected. The counter is decrement by 1 on each cycle until it reaches zero. Only when the counter is at zero is the data seen as valid and available by the processor pipeline.

ADDITIONAL ASPECTS

The mechanism described allows for timing compensation between memory accesses. If the Overlay system was extended to cover both code and data access this mechanism would potentially be useful in compensating for timing differences associated with Flash-to-Flash overlay as required by various software-over-the air (SOTA) implementations.

In the case where the target and overlay memories are the same memory this mechanism can be used to add additional delay cycles to every access from the memory. This could be potentially useful for tuning performance or power consumption.

The overlay system including this proposal is included within the area of duplication for locksteped implementations. This supports safe operation of the delay timer.

Embodiments fulfil a customer requirement that they should be able to overlay flash memory without the system timing or real time behavior being impacted.

A simple embodiment comprises a programmable delay able to compensate for the timing difference between memory accesses to different memory ranges during data access overlay.

As an alternative, a simple system could be produced that delays all overlay memory accesses by a fixed amount but this would not have the resolution of this proposal.

In addition, it should be noted that a crossbar circuit may also be used for an interconnection between a plurality of processors and a plurality of memories, for example instead of a bus. The crossbar circuit may comprise multiple (for example, parallel) data paths, which may be used to simultaneously to establish multiple connections, each connection, for example, between a processor and a memory. The overlay mechanism may, for example, be coupled between a processor core and a crossbar switch (which selectable connects a processor with one out of a plurality of communication paths of the crossbar). The overlay mechanism may be configured to consider characteristics of the crossbar, like, for example, possible crossbar contention. In so far, embodiments using a crossbar are similar to embodiments using a bus, or using a bus system (wherein a contention in a crossbar-based system is typically smaller than a contention in a bus-based system). In other words, the features and functionalities described herein with respect to a system using a bus also apply to a system using a crossbar, and can be used individually or in combination.

The invention claimed is:

1. A device, comprising:

processing circuitry comprising an overlay mechanism configured to redirect an access which is directed to a first memory location to a second memory location, wherein the overlay mechanism is configured to delay access to the second memory location in the case of a redirection, wherein the overlay mechanism is configured to adapt the delay depending on access times of memory locations, and wherein the overlay mechanism is configured to detect if a second access to the first memory location follows a first access to the first memory location, causing a changed access time to the first memory location when accessing successional memory locations of the first memory location, and in this case adapting, when accessing the first memory location with the second access, the delay to the changed access time of the first memory location, wherein the second memory location is physically separate from the first memory location.

2. The device according to claim 1, wherein the first memory location is a flash-type memory and/or the second memory location is a SRAM-type memory.

3. The device according to claim 1, wherein the delay of the overlay mechanism is programmable.

4. The device according to claim 1, wherein the delay of the overlay mechanism is configured to compensate at least partially for a difference between access times of the first memory location and of the second memory location.

5. The device according to claim 1, wherein the device is connectable to the first memory location and the second memory location by at least one bus or by at least one crossbar.

6. The device according to claim 5, wherein the overlay mechanism is configured to delay a processing operation of the processing circuitry requesting access to the first memory location or to delay a forwarding of data from the bus or from the crossbar to the processing circuitry, to thereby delay access to the second memory location.

7. The device according to claim 6, wherein the overlay mechanism is configured to delay a processing operation by stalling at least one cycle of the processing circuitry.

8. The device according to claim 1, wherein the overlay mechanism is configured to redirect an access to a first target memory range in the first memory location to a first overlay memory range in the second memory location, and to redirect an access to a second target memory range to a second overlay memory range, and wherein the overlay mechanism is configured to apply a first delay in case of an access to the first target memory range and to apply a second delay, which is different from the first delay, in case of an access to the second target memory range in case of a redirection.

9. The device according to claim 1, wherein the overlay mechanism is configured to extend an access time to the second memory location to be equal or larger to a target access time in case of a redirection.

10. The device according to claim 9, wherein an access time to the first memory location is longer than an undelayed access time to the second memory location, and wherein the target access time is equal to or larger than the access time of the first memory location.

11. The device according to claim 9, wherein the target access time is programmable.

12. The device according to claim 1, wherein the overlay mechanism is configured to compensate for varying undelayed access times to the second memory location.

13. The device according to claim 1, wherein the overlay mechanism is configured to start or initialize an incrementing or decrementing counter in response to a detection that an overlay operation is performed, and wherein the overlay mechanism is configured to signal data received from the second memory location as being available for a processor of the device in response to a detection that a predetermined number of clock cycles has elapsed since the starting or initializing of the counter.

14. A device, comprising:

processing circuitry comprising an overlay mechanism configured to redirect an access which is directed to a first memory location to a second memory location, wherein the overlay mechanism is configured to delay access to the second memory location in the case of a redirection, wherein the overlay mechanism is configured to adapt the delay depending on access times of memory locations, wherein the overlay mechanism is configured to extend an access time to the second memory location to be equal or larger to a target access time in case of a redirection, wherein an access time to the first memory location is longer than an undelayed access time to the second memory location, and wherein the target access time is equal to or larger than the access time of the first memory location, and wherein the overlay mechanism is configured to detect if a second access to the first memory location follows a first access to the first memory location, causing a changed access time to the first memory location when accessing successional memory locations of the first memory location, and in this case adapting, when accessing the first memory location with the second access, the delay to the changed access time of the first memory location.

15. The device according to claim 14, wherein the first memory location is a flash-type memory and/or the second memory location is a SRAM-type memory.

16. The device according to claim 14, wherein the delay of the overlay mechanism is programmable.

17. The device according to claim 14, wherein the delay of the overlay mechanism is configured to compensate at least partially for a difference between access times of the first memory location and of the second memory location.

18. The device according to claim 14, wherein the device is connectable to the first memory location and the second memory location by at least one bus or by at least one crossbar.

19. The device according to claim 18, wherein the overlay mechanism is configured to delay a processing operation of the processing circuitry requesting access to the first memory location or to delay a forwarding of data from the bus or from the crossbar to the processing circuitry, to thereby delay access to the second memory location.

20. The device according to claim 19, wherein the overlay mechanism is configured to delay a processing operation by stalling at least one cycle of the processing circuitry.

* * * * *